(12) United States Patent
Kolditz et al.

(10) Patent No.: US 7,781,466 B2
(45) Date of Patent: Aug. 24, 2010

(54) PREPARATION FOR THE FUNGICIDAL AND ALGICIDAL FINISH OF ALKALINE COATING COMPOSITIONS

(75) Inventors: Petra Kolditz, Hamburg (DE); Klaus Weber, Hamburg (DE); Ralf Gradtke, Tornesch (DE); Wolfgang Beilfuss, Hamburg (DE)

(73) Assignee: Air Liquide Sante (International), Paris (FR)

( * ) Notice: Subject to any disclaimer, the term of this patent is extended or adjusted under 35 U.S.C. 154(b) by 999 days.

(21) Appl. No.: 11/524,825

(22) Filed: Sep. 21, 2006

(65) Prior Publication Data

US 2007/0093538 A1 Apr. 26, 2007

(30) Foreign Application Priority Data

Sep. 21, 2005 (DE) .................. 10 2005 045 129

(51) Int. Cl.
*A01N 33/12* (2006.01)
*A01N 43/80* (2006.01)
*C09D 5/14* (2006.01)
*C09D 5/16* (2006.01)

(52) U.S. Cl. .................. 514/372; 514/373; 514/371; 514/360; 514/362; 514/643; 252/188.21; 252/188.24; 106/15.05; 106/18.11

(58) Field of Classification Search .................. 514/360, 514/371, 372, 373, 642, 643; 106/18.11, 106/15.05

See application file for complete search history.

(56) References Cited

U.S. PATENT DOCUMENTS

| 6,846,492 | B2 * | 1/2005 | Haap et al. ................. 424/405 |
| 2005/0101487 | A1 * | 5/2005 | Beilfuss et al. ............. 504/134 |
| 2008/0076803 | A1 * | 3/2008 | Beilfuss et al. ............. 514/345 |
| 2008/0300283 | A1 * | 12/2008 | Beilfuss et al. ............. 514/345 |

FOREIGN PATENT DOCUMENTS

| DE | 42 42 389 | | 6/1994 |
| DE | 197 05 085 | | 8/1998 |
| DE | 198 10 819 | A1 | 9/1999 |
| DE | 101 44 187 | | 6/2003 |
| DE | 102 37 264 | | 3/2004 |
| EP | 1 290 943 | | 3/2003 |
| EP | 1 290 943 | A1 | 3/2003 |
| EP | 1 389 424 | A1 | 2/2004 |
| WO | WO 98 33380 | | 8/1998 |
| WO | WO 02/28952 | A1 | 4/2002 |
| WO | WO 03/020036 | A1 | 3/2003 |

\* cited by examiner

*Primary Examiner*—Joseph D Anthony
(74) *Attorney, Agent, or Firm*—Young & Thompson

(57) ABSTRACT

The invention relates to a preservative comprising at least one isothiazolone, at least one quaternary ammonium compound, and at least one stabilizer selected from the group of sulphite salts, hydrogen sulphite salts, sulphite-releasing compounds and hydrogen-sulphite-releasing compounds, the presence of algicidal triazine being ruled out. The preservative inhibits the growth of fungi, algae and bacteria on or in alkaline coating compositions. The invention furthermore relates to a process for the preparation of the preservative, to its use in a coating composition, and to the preserved composition.

8 Claims, No Drawings

PREPARATION FOR THE FUNGICIDAL AND ALGICIDAL FINISH OF ALKALINE COATING COMPOSITIONS

CROSS REFERENCE TO RELATED APPLICATIONS

This application claims the benefit of priority under 35 U.S.C. §119 (a) and (b) to German Application No. 10 2005 045 129.2, filed Sep. 21, 2005, the entire contents of which are incorporated herein by reference.

BACKGROUND

The invention relates to a preservative which inhibits the growth of fungi, algae and bacteria on or in alkaline coating compositions. The invention furthermore relates to a process for the preparation of the preservative, its use in a coating composition, and the preserved composition.

Film preservatives protect coating compositions such as paints, colors, renders, varnishes, plastics, fibers, fillers and sealants from microbial attack and decomposition. For finishing such compositions for the exterior and interior sector, a series of microbicidal (bactericidal, fungicidal and algicidal) active substances are employed which generally offer good protection when employed on neutral or weakly alkaline surfaces. Examples of known biocides this field of application are fungicides such as 2-methoxycarbonylaminobenzimidazole(carbendazim), 2-mercaptopyridine N-oxide (in particular the zinc salt: zinc pyrithion) and iodopropynyl butylcarbamate (IPBC) or algicides such as 1,1-dimethyl-3-(3,4-dichlorophenyl)urea (diuron), methylthio-4-t-butylamino-6-cyclopropylamino-s-triazine (Irgarol 1051, Mott), and $N^2$-tert-butyl-$N^4$-ethyl-6-methylthio-1,3,5-triazine-2,4-diamine (terbutryne). These known microbicides are described, inter alia, in the Offenlegungsschriften DE 42 42 389 A1 and DE 197 05 085 A1.

The microbicides employed in coating compositions must be active against fungi (e.g. *Aspergillus niger, Penicillim funiculosum*)—including *Alternaria* species—and algae. In practice, it has therefore proved to be advantageous to use active substance mixtures which cover a broad spectrum of activity. To close the *Alternaria* gap, film preservatives also employ isothiazolon-3-ones (isothiazolones), for example N-octylisothiazolone, which is obtainable in the form of an approximately 45% strength solution in 1,2-propylene glycol under the name Kathon 893.

There are, furthermore, known products with the active substance combination terbutryne+Kathon 893. However, these products contain large amounts of solvent or emulsifier, which does not meet the demand of the market for products which are low in, or free from, solvents (VOCs). Also, the stability of this product is unsatisfactory. Thus, studies by applicant have demonstrated that aqueous dispersions comprising Kathon 893 and terbutryne are not sufficiently storage-stable. For example, while the combination of terbutryne and Kathon 893 (or the solvent-free variant Kathon 893 T) can initially be converted into a homogeneous, whitish, aqueous dispersion, such an aqueous dispersion is not sufficiently stable. After a certain time has elapsed (i.e. after approximately 6 months at room temperature), the consistency changes, and an inhomogeneous, grainy dispersion is formed. An inhomogeneous dispersion, however, tends to form sediments and to result in an uneven distribution of the active substance in the container. Such a product cannot be used in colors, renders and other coatings since the consistency of the end product is adversely affected and there is a risk of inappropriate dosage.

DE 101 44 187 A1 relates to a preservative, in particular for alkaline coatings, which comprises one or more quaternary ammonium compounds and one or more specific alkalizing agents. DE 102 37 264 A1 discloses an aqueous dispersion with fungicidal and algicidal activity which comprises algicidal triazine, fungicidal isothiazolone and, as dispersion stabilizer, for example sulphite salt. While these compositions have a good to sufficiently good microbicidal activity in coating compositions, their ability to be incorporated into the coating materials and the fact that they adversely affect the processibility, for example of the renders, is disadvantageous. Moreover, these compositions sometimes lead to an undesired increase in the viscosity of the preserved coating compositions.

In the presence of ferrous building materials, zinc pyrithion furthermore readily results in discolorations and, as the result of hydrolysis, becomes soluble on highly-alkaline substrates and therefore leaches readily. Compositions containing iodopropynyl butylcarbamate discolor readily, in particular when exposed to UV, are not resistant to alkali and are not sufficiently resistant to leaching. Higher concentrations of benzalkonium chloride and benzalkonium waterglass show a pronounced increase in the viscosity in the preserved render. In certain combinations with other preservatives, grey staining of the microbicidally finished coating compositions is also observed.

The present invention is therefore based on the object of providing a preservative with good bactericidal, fungicidal and algicidal activity for use in coating compositions.

The preservative should be microbicidally active against fungi and algae, including *Alternaria* species, resistant to leaching, even under (highly) alkaline conditions, that is to say also suitable for alkaline renders, and capable of being used on alkaline surfaces, in particular highly-alkaline surfaces, no tendency to develop discolorations, in particular when exposed to UV, capable of being formulated as a liquid concentrate (for example a dispersion) (i.e. it should be capable of being pumped, which is necessary as the result of the use of automatic metering systems), foam-free, have a pH of not more than 10 in the container, storage-stable at low and high temperatures, including tropical conditions, compatible with the other components of the coating composition (for example paint, render), when incorporated into a coating material, not result in an appreciable change in viscosity (because the good applicability of the render must be ensured) and not be an environmental hazard in the coating composition, i.e. the behavior of the coating composition in waste water should not be more disadvantageous than water hazard class 2.

Surprisingly, it has now been found that the problems of the prior art can be solved by a preservative comprising a) at least one isothiazolone, b) at least one quaternary ammonium compound and c) at least one stabilizer selected from the group of sulphite salts, hydrogen sulphite salts, sulphite-releasing compounds and hydrogen-sulphite-releasing compounds, the presence of algicidal triazine in the preservative being ruled out. The invention is based inter alia on the fact that it has surprisingly been found that the algicidal activity of the preservative according to the invention is good, even in the absence of an algicidal triazine.

Isothiazolone

Isothiazolones which are employed in accordance with the invention are isothiazolin-3-ones and selected from amongst N-octylisothiazolone, N-methylisothiazolone, 4,5-dichloro-N-octylisothiazolone, benzoisothiazolone and N-butylbenzoisothiazolone. Kathon 893 is especially preferred.

Quaternary Ammonium Compound

The preservative according to the invention comprises at least one quaternary ammonium compound. A quaternary ammonium compound can be, for example, a betaine or a zwitterionic compound. Preferred in this context are quaternary ammonium compounds which exist in aqueous solution in such a form that they are partially or fully dissociated into anion(s) and cation(s) (quaternary ammonium salts).

Preferred quaternary ammonium salts are described by the formulae $[R^1R^2R^3R^4N]^+[X]^-$ and $[N-R^5\text{-pyridinium}]^+[X]^-$, where $R^1$ to $R^5$ can be identical or different and are selected from amongst $C_1$-to $C_{30}$-alkyl, -alkenyl and -aryl and mixed groups which may contain one or more atoms selected from amongst O, S, N and P, it also being possible for one or more $R^1$ to $R^4$ to be H, with the proviso that at least one of the groups $R^1$ to $R^4$ is other than H. X is an anion (of an inorganic or organic acid). In this context, both anion and cation of the quaternary ammonium salt can be polyvalent ions, resulting in a stoichiometry of $[A^{(n+)}]_m[K^{(m+)}]_n$.

Quaternary ammonium cations which are preferably employed in accordance with the invention are $[R^1N(CH_3)_3]^+[X]^-$, $[R^1NH_3]^+[X]^-$, $[R^1(\text{aryl}CH_2)NH_2]^+[X]^-$, $[R^1(\text{aryl}CH_2)N(CH_3)_2]^+[X]^-$, $[R^1R^2N(CH_3)_2]^+[X]^-$ and $[N-R^5\text{-pyridinium}]^+[X]^-$, where $R^1$, $R^2$ and $R^5$ independently of one another are selected amongst $C_1$-to $C_{30}$-alkyl, $C_6$-to $C_{12}$-aryl and $-(CH_2-CHR^6O)_n-R^7$, where n is a number from 1 to 20 and $R^6$ and $R^7$ which can be identical or different, are H and/or $C_1$-to $C_4$-alkyl, and aryl denotes an aryl group which is optionally substituted.

Examples of cations of the quaternary ammonium salts which are employed in accordance with the invention correspond to the formula $[R^1N(CH_3)_3]^+$, where $R^1$ is a $C_6$-to $C_{20}$-alkyl, -hydroxyalkyl or polyoxyalkyl group or an optionally substituted aromatic radical having 6 to 12 carbon atoms. Further preferred cations of the quaternary ammonium salts according to the invention are $C_8$-to $C_{18}$-alkylbenzylammonium, benzalkonium, didecyl and dioctyldimethylammonium, didecylmethyl-poly(oxyethyl)ammonium, cetylpyridinium, cetyltrimethylammonium and benzyl-fatty-alkyl-bis(hydroxyethyl)ammonium and mixtures of these, the preservative especially preferably comprising mixtures of two, three and four of these preferred cations, such as mixtures of benzalkonium salts with dialkyldimethylammonium salts. In this context, the cation may exist as a polymer, as is the case for example in polyhexamethylene biguanide (Vantocil IB).

Examples of anions and classes of anions of the quaternary ammonium salts employed in accordance with the invention are hydroxide, sulphate, hydrogen sulphate, methosulphate, ethosulphate, lauryl sulphate, lauryl ether sulphate, cellulose sulphate, sulphamate, halide (fluoride, chloride, bromide, iodide), nitrite, nitrate, orthosilicate (for example sodium orthosilicate, potassium orthosilicate, magnesium orthosilicate and aluminium orthosilicate), disilicate, metasilicate, layer silicate such as hectorite, bentonite, montmorillonite, smectite, carbonate, hydrogencarbonate, phosphate, alkyl phosphate, metaphosphate, polyphosphate, phosphonate, thiocyanate (rhodanide), zincate, aluminate, alumosilicate (for example zeolite), thiosulphuric esters (for example the Bunte salts from DE-A41 22 962 and DE-A-3 307 733), carboxylic acid salt such as benzoate, lactate, acetate, propionate, citrate, succinate, glutarate, adipate, toluenesulphonate (tosylate), salicylate, mercapto compound such as 2-mercaptobenzothiazole, 2-mercaptopyridine N-oxide, dithiocarbamate, fatty acid anion such as stearate, laureate, 2-ethylhexanoate, saccharinate, sulphonate such as alkylbenzenesulphonate, alkylsulphonate and phenolate such as phenylphenolate. Moreover, anions which can be used are also known anion surfactants which are capable of forming neutral salts with the cations of the quaternary ammonium salts (quat-anion surfactant complexes). Especially preferred anion is chloride.

In the context of the invention, the definition of isothiazolones also includes the combination of isothiazoline-3-one and sulphites in solution which forms the so-called Bunte salts, which are thiosulfuric acid derivatives. These Bunte salts are adducts of isothiazoline-3-one in equilibrium with the starting combination of isothiazoline-3-one and sulphites. For instance, in a solution prepared by combining isothiazoline-3-one and sulphite, the isothiazoline-3-one is quantitatively found using analytical techniques such as HPLC.

Examples of especially preferred quaternary ammonium salts are benzalkonium salts, for example benzalkonium chloride, benzalkonium thiocyanate, benzalkonium silicate, didecyidimethylammonium salts and polyhexamethylene biguanide salts. The use of a 50% strength aqueous benzalkonium chloride solution is especially preferred.

Stabilizer

Stabilizers according to the invention are selected from the group consisting of sulphite salts, hydrogen sulphite salts, sulphite-releasing compounds and hydrogen-sulphite-releasing compounds. Examples are alkali metal metasulphites (for example $Na_2S_2O_5$, $K_2S_2O_5$), alkali metal hydrogen sulphites or other metal salts or metal salt complexes of these sulphites, furthermore substances which release sulphite in solution, such as bisulphites of organic carbonyl compounds (for example aldehyde bisulphites). The use of sodium bisulphite is especially preferred.

Preferred quantities and mixing ratios of the components a) to c) are (in % by weight):

| a) | 1-30 | 2-25 | 5-20 | 8-18 | 10-14 |
|----|------|------|------|------|-------|
| b) | 2-60 | 5-55 | 10-50 | 20-40 | 24-33 |
| c) | 0.5-15 | 1-12 | 2-10 | 3-8 | 4-7 |

If appropriate, the preservative according to the invention is present in d) alcohol-based and/or e) aqueous-based form and additionally comprises (in % by weight):

| d) | 1-30 | 2-25 | 5-20 | 10-18 | 12-16 |
|----|------|------|------|-------|-------|
| e) | 3-80 | 6-70 | 10-60 | 20-55 | 30-50 |

In a preferred embodiment, the preservative is present on 2 aqueous and/or alcoholic base and comprises
  a) 8 to 18% by weight, preferably 10 to 14% by weight, of isothiazolone,
  b) 20 to 40% by weight, preferably 24 to 33% by weight, of quaternary ammonium compound and c) 3 to 8% by weight, preferably 4 to 7% by weight, of stabilizer and
d) 10 to 18% by weight, preferably 12 to 16% by weight, of aliphatic alcohol and/or
e) 20 to 55% by weight, preferably 30 to 50% by weight, of water.

In a preferred embodiment, the preservative according to the invention is present in the form of a dispersion. Suitable additives are known to the skilled worker. In particular, it has, surprisingly, been found that aqueous dispersions which comprise a) isothiazolone and b) quaternary ammonium compound can be stabilized in a dispersion by means of the abovementioned components c). The improvement in stability manifests itself inter alia in the fact that the preservatives remain homogeneous longer than would be the case without the addition of the abovementioned stabilizers.

Besides the components a), b) and c) and, if appropriate, d) and/or e) one or more functional additives may be added to the preservatives according to the invention. Examples of suitable additives are:

fillers, for example kaolin, silica gel (for example Aerosil 200), calcium carbonate, titanium dioxide,
solvents, for example alcohols, glycols, glycol ethers such as triethylene glycol, propylene glycol, butyl diglycol, humectants,
thickeners/viscosity modifiers, for example hydroxyethylcellulose,
wetting agents, for example nonionic surfactants,
dispersants, pigment dispersing distributors and
alkalizing agents, for example alkali metal waterglass, alkali metal hydroxides.

Preferred in this context are preservatives which are free from zinc pyrithion and/or carbendazim.

Moreover, the invention relates to a process for the preparation of the preservative according to the invention in which
water is initially introduced,
stabilizer is incorporated (for example by stirring),
isothiazolone is incorporated (for example by stirring),
silica gel is incorporated,
quaternary ammonium compound (for example in the form of a 50% strength aqueous benzalkonium chloride solution) is added to the mixture and
the components are stirred to give a white paste.

Moreover, the preservative according to the invention can also comprise further active substances, for example iodopropynyl butylcarbamate (IPBC), copper pyrithion, tebuconazole, ipconazole, bethoxazin, alkali metal thiocyanates, copper salts, zinc salts and/or zinc oxides.

The invention furthermore relates to the use of the preservative according to the invention in or on industrial materials for the interior or exterior sector, in particular to the use for the microbicidal finishing of paints, colors, renders, varnishes, fillers, sealants, plastics, compound materials, wood, concrete, stone, paper, board, leather, textiles, glues and adhesives.

Suitable dispersions as basic materials for coating compositions are described for example in DE-A-37 11 680 and EP-A-0 328 335 and in Karsten, Lackrohstoff-Tabellen [Tables of base materials for varnishes], Kurt Vinzenz Verlag 2000, in particular on pages 364 (poly(meth)acrylate homopolymer and copolymer dispersions) and 451 (silicone-based dispersions) in the last-mentioned publication. Preferred paints and renders which comprise polymer dispersions or synthetic resin dispersions are:

acrylate- or all-acrylate-based paints and renders with a polymer content of not more than 50% by weight, preferably not more than 30% by weight and especially preferably not more than 15% by weight,
acrylic/styrene-copolymer-based paints and renders with a polymer content of not more than 50% by weight, preferably not more than 30% by weight and especially preferably not more than 15% by weight,
silicone-resin-based paints and renders with a polymer content of not more than 50% by weight, preferably not more than 30% by weight and especially preferably not more than 15% by weight,
silicate (for example cement)-based paints and renders based on potassium waterglass, if appropriate together with small amounts (preferably not more than 10% by weight, especially preferably 5% by weight) of all-acrylate dispersions or acrylic/styrene copolymer dispersions.

While the preservative according to the invention is preferably employed in the preparation of a coating composition which comprises synthetic resin or polymer dispersions, the presence of such a dispersion is not imperative, which is why, in an alternative embodiment, the coating composition which comprises the preservative according to the invention is free from synthetic-resin or polymer dispersion.

In a preferred embodiment, the composition which has been imparted a microbicidal (in particular fungicidal) finish by the preservative has a pH of at least 9, more preferably 10.0 to 13.5, in particular 10.5 to 13, for example 11 to 12.5 and 11.2 to 11.8.

Preferably, a composition is formulated in such a way that it comprises 0.05 to 10% by weight, more preferably 0.1 to 5% by weight and in particular 0.2 to 2% by weight, for example 0.3 to 1.0% by weight, of the preservative, a use concentration of not more 0.4% by weight being preferred.

In a preferred embodiment of the invention, a composition which is finished in accordance with the invention with preservative is present in the form of a lacquer or a paint for the interior or exterior sector. In such a case, such a composition comprises, in addition to the synthetic resin dispersion (as organic binder) and the preservative according to the invention, one or more other organic binders, pigments, fillers and additives, the term "additives" encompassing thickeners, wetting agents, dispersants, antifoams, adhesion promoters, surface modifiers such as slip additives or mattifying agents, flow assistants and film-forming adjuvants, desiccants, anti-skinning agents, light stabilizers, corrosion inhibitors, flame retardants and pack preservatives. Examples of compositions which are finished in accordance with the invention with preservative and which are present in the form of a lacquer are (grouping by type of binder): all-acrylate dispersion lacquers, styrene acrylate dispersion lacquers, alkyd resin dispersion lacquers and polyurethane dispersion lacquers. Suitable examples of compositions which are finished in accordance with the invention with preservative and which are present in the form of a paint are (grouping by type of binder): all-acrylate dispersion paints, styrene acrylate dispersion paints, silicone resin dispersion paints, silicone-resin-modified all-acrylate dispersion paints, silicate paints and synthetic-resin-modified silicate paints.

In a further embodiment, a preservative according to the invention is incorporated into a material which has already been brought to an alkaline pH, for example a finished render, in particular a silicate render. However, a composition which has been finished in accordance with the invention can also be present in the form of a compound which is used in the preparation of a render (render base).

In the present context, the term "render" comprises both wet renders, i.e. coating materials in the liquid processing state, such as synthetic-resin renders, but also dry renders, i.e. pulverulent dry render preparations which, mixed with water, are brought into a processible liquid state, such as lime wash, gypsum plaster render or cement render. Examples of components of compositions which are finished in accordance with the invention with preservative and which are present in the form of a render are lime, cement, gypsum, anhydrite, organic polymers or copolymers as binders, additives such as sands and additives which modify the properties of the renders, such as air entrainers, liquefactants, accelerator additives, retarding agents, sealing adjuvants, antifreeze agents and plastifying polymer additives (see also Brasholz, Handbuch der Anstrich-Beschichtungstechnik [Handbook of Paint Coating Techniques], Bauverlag GmbH, 2nd edition 1989; Römpp-Lexikon Lacke und Druckfarben [Römpp's Dictionary of Paints and Inks], Georg Thieme Verlag 1998, keyword "Putze" [renders]). Examples of compositions which are finished in accordance with the invention with preservative and which are present in the form of a render are (grouping by type of binder) inorganically bound renders such as silicate render, lime wash, gypsum plaster render, cement render and synthetic-resin-modified types of these classes, and organically bound renders or synthetic resin renders such as all-acrylate dispersion render, styrene acrylate dispersion render, acrylate copolymer dispersion render, silicone resin dispersion render, silicone-resin-modified all-acrylate dispersion render, polyvinyl acetate dispersion render, polyvinyl acetate copolymer dispersion render and polyvinyl propionate/acrylate copolymer dispersion render.

The preservatives and compositions according to the invention meet the above requirements. Thus, the preservatives are inexpensive and in some cases commercially available or can be prepared readily from commercially available substances by simple methods and can be introduced into the market without problems because substances are used which have already been studied and evaluated with regard to human toxicology and ecotoxicology.

Surprisingly, a good to sufficient compatibility (long-term stability) of the quaternary ammonium compounds with the other constituents of the composition and/or in contact with the alkaline substrate have also been found.

In comparison with the preservatives of DE 101 44 187 A1, preservatives according to the invention are more resistant to leaching, more resistant to alkali and show less discoloration in the coating composition, they are more effective and can be incorporated more easily into coating materials (for example renders) (when incorporated into coating materials, they exhibit, for example, a smaller change in viscosity, which makes procedures at building sites less complicated), they are more compatible with other active substances and functional additives, and they have good storage stability, even in the form of a concentrate. It is not imperative that the preservative comprises alkalizing agents (which has advantages for the handling), it is homogeneous, can be spread readily, even as a mixture with silica gel, and also has no adverse effects on the spreadability of a microbicidally finished render.

Moreover, the preservative according to the invention has pronounced advantages regarding the activity, stability and use properties (no increased viscosity when incorporated into a coating material) in comparison with the abovementioned agents of DE 101 44 187 A1 and DE 102 37 264 A1.

The advantages of the invention can be seen in particular from the examples which follow. All parts are by weight.

EXAMPLES

Example 1

Preservative A According to the Invention, and Methods

| Components of preservative A | % by weight |
| --- | --- |
| Purified water | 10.8 |
| Sodium bisulphite | 5.6 |
| Kathon 893 (46.0% strength in 1,2-propylene glycol) | 26.5 |
| Aerosil 200 | 1.0 |
| Benzalkonium chloride (50% strength in water) | 56.1 |

Purified water is first introduced into the reaction vessel, and sodium bisulphite is added. The mixture is stirred for approximately 10 minutes until almost all of the solid is dissolved. Then, Kathon 893 is added, and the mixture is stirred for 10 minutes. The temperature of the solution climbs slightly during this process. Thereafter, Aerosil 200 is added and the mixture is stirred until everything is distributed homogeneously. Finally, benzalkonium chloride is added and stirring is continued for approximately 30 minutes. This gives a white paste (preservative A).

The unfinished material (commercially available render, pH 11.5) is treated, in separate batches, with different concentrations of the preservative A according to the invention.

The tests for the fungicidal and algistatic finishing were carried out by the standard test methods described hereinbelow. *Alternaria alternata* (DSM 62010) was concomitantly tested as the 3rd test microorganism.

The test was carried out once after the samples had been prepared and then after storage in wet render for 3 months or 5 months.

Test Method 1

Determination of the Resistance to Fungal Attack

Field of Application

Laboratory method for determining the resistance of facade coats to fungal attack. For this method, facade coats on standardized paper were used as test substrate, and *Aspergillus niger* (AN, ATCC 6275), *Penicillium funiculosum* (PF, ATCC 36839) and *Alternaria alternata* (AL) were used as test fungi.

The experiments were carried out in Petri dishes on dextrose media.

Sample Preparation 1000 g of the material to be finished were, in separate batches, mixed with various concentrations of the test fungicide and homogenized using a suitable stirrer.

Preparation of the Test Objects

Paper supports (Schleicher & Schüll No. 2589 B/X 24078) 90×270 mm in size are coated with the test material. The paint or render samples are applied as a coat to wet-layer thickness of 250 μm, using a knife. The knife must have an opening of at least 6.5 cm in width. In the case of renders, the layer thickness depends on the particle size, as is the case under practice conditions. The coated supports, hereinbelow referred to as test specimens, are subsequently dried for 5 days in a horizontal position.

Pretreatment of the Test Specimens

The pretreatment of the test specimens is intended to simulate the removal of microbicides as the result of the impact of the weather, which is possible under practice conditions. To this end, the test specimens are leached for 72 hours (336 hours in the case of renders) in running tap water at 15±5° C. at a flow rate of 1 l/min and then dried for 2 days. The cross-section of the container for the leaching treatment in the direction of the flow should be 1000±500 cm². Then, samples of diameter 5 cm are punched from the pretreated test specimens and sterilized in a $Co^{60}$ source using at least 10 kGy.

Test Protocol

Inoculation and Incubation

The Sabouraud dextrose agar which had solidified in the Petri dish is inoculated with 0.2 ml of spore suspension ($10^7$ spores/ml) and plated using a sterile Drigalski spatula or a sterile glass rod which forms an angle.

Thereafter, the pretreated samples are placed uniformly on the surface of the inoculated medium, using tweezers. Care must be taken that the samples are fully in contact with the surface of the medium. The media are subsequently incubated for three weeks at 30±2° C.

Evaluation

After one, two and three weeks, the samples are examined for fungal growth. They are evaluated visually or, if required to rule out contaminations, using a magnifying glass. If contamination is observed in a degree which substantially interferes with the evaluation, the experiment cannot be evaluated and must be repeated. The evaluation of the samples is based on the following evaluation scale:

| | | |
|---|---|---|
| 0 = | Entire plate free from colonization to colonization only at the edge of the sample (not more than 1%) | Test criteria met |
| 1 = | Colonization of the sample from the edge (less than 25%) | Limited protection |
| 2 = | Sample surface colonized by individual colonies (25-75%) | |
| 3 = | Sample surface extensively colonized (75% and more, but not the entire surface) | |
| 4 = | All of the sample surface colonized (100%) | No protection |

Test Method 2

Determination of the Resistance to Colonization by Algae

Field of Application

Laboratory method for determining the resistance of facade coats to colonization by algae. In this method, facade coats on standardized paper are used as the test substrate, and *Scenedesmus cavuolatus* (CS, *Chlorella fusca*) as the test alga.

The experiments are carried out in Petri dishes on media for algae.

Sample Preparation 1000 g of the material to be finished were, in separate batches, mixed with various concentrations of the test microbicide and homogenized using a suitable stirrer.

Preparation of the Test Objects

Paper supports (Schleicher & Schüll No. 2589 B/X 24078) 90×270 mm in size are coated with the test material. The paint or render samples are applied as a coat to wet-layer thickness of 250 µm, using a knife. The knife must have an opening of at least 6.5 cm in width. In the case of renders, the layer thickness depends on the particle size, as is the case under practice conditions. The coated supports, hereinbelow referred to as test specimens, are subsequently dried for 5 days in a horizontal position.

Pretreatment of the Test Specimens

The pretreatment of the test specimens is intended to simulate the removal of microbicides as the result of the impact of the weather, which is possible under practice conditions. To this end, the test specimens are leached for 72 hours (336 hours in the case of renders) in running tap water at 15±5° C. at a flow rate of 1 l/min and then dried for 2 days. The cross-section of the container for the leaching treatment in the direction of the flow should be 1000±500 cm². Then, samples of diameter 5 cm are punched from the pretreated test specimens and sterilized in a $Co^{60}$ source using at least 10 kGy.

Test Protocol

Inoculation and Incubation

The samples are placed under sterile conditions on the media for algae and inoculated in the middle with 0.5 ml of each algal suspension.

The mixture of the algal suspension is distributed on the surface using a Drigalski spatula or an angled sterile glass rod.

During the growth phase at 22±2° C., the coated samples are exposed, in the Petri dishes, to light with an intensity of about 1000 Lux (conventional fluorescent tubes, type D 67 daylight). A cycle of in each case 12 hours exposure and 12 hours storage in the dark is used.

Evaluation

The colonization of the samples with algae is examined and evaluated after 2 weeks. The evaluation is carried out visually. The evaluation is based on the following evaluation scale:

Group 1 (IZ)

No algal colonization on the test specimens.

Formation of an inhibitory zone (IZ=diameter of the inhibitory zone in mm) or algal colonization on the medium right to the edge of the test specimen.

Paints of these groups can be characterized by the term "effectively finished against colonization by algae".

Group 2 (C)

Visible colonization by algae on the test specimen.

−=no colonization

+=some colonization

++=moderate colonization

+++=pronounced colonization

Example 2

Results

Fungicidal finish

Without storage

| | Without leaching | | | Leaching for 72 h | | |
|---|---|---|---|---|---|---|
| | 1 week | 2 weeks | 3 weeks | 1 week | 2 weeks | 3 weeks |
| Test microorganism (*Penicillium funiculosum*) | | | | | | |
| Render, no preservative | 0 | 0 | 0 | 2 | 3 | 3 |
| +0.20% A | 0 | 0 | 0 | 0 | 0 | 0 |
| +0.30% A | 0 | 0 | 0 | 0 | 0 | 0 |
| +0.40% A | 0 | 0 | 0 | 0 | 0 | 0 |
| Test microorganism (*Aspergillus niger*) | | | | | | |
| Render, no preservative | 2 | 2 | 2 | 3 | 4 | 4 |
| +0.20% A | 0 | 0 | 0 | 0 | 0 | 0 |
| +0.30% A | 0 | 0 | 0 | 0 | 0 | 0 |
| +0.40% A | 0 | 0 | 0 | 0 | 0 | 0 |
| Test microorganism (*Alternaria alternata*) | | | | | | |
| Render, no preservative | 3 | 4 | 4 | 2 | 3 | 3 |
| +0.20% A | 0 | 0 | 0 | 3 | 3 | 3 |
| +0.30% A | 0 | 0 | 0 | 0 | 0 | 0 |
| +0.40% A | 0 | 0 | 0 | 0 | 0 | 0 |

3 month storage

| | Without leaching | | | Leaching for 72 h | | |
|---|---|---|---|---|---|---|
| | 1 week | 2 weeks | 3 weeks | 1 week | 2 weeks | 3 weeks |
| Test microorganism (*Penicillium funiculosum*) | | | | | | |
| Render, no preservative | 2 | 2 | 2 | 2 | 3 | 3 |
| +0.20% A | 0 | 0 | 0 | 0 | 0 | 0 |
| +0.30% A | 0 | 0 | 0 | 0 | 0 | 0 |
| +0.40% A | 0 | 0 | 0 | 0 | 0 | 0 |
| Test microorganism (*Aspergillus niger*) | | | | | | |
| Render, no preservative | 3 | 3 | 3 | 3 | 3 | 3 |
| +0.20% A | 0 | 0 | 0 | 0 | 0 | 0 |
| +0.30% A | 0 | 0 | 0 | 0 | 0 | 0 |
| +0.40% A | 0 | 0 | 0 | 0 | 0 | 0 |
| Test microorganism (*Alternaria alternata*) | | | | | | |
| Render, no preservative | 4 | 4 | 4 | 3 | 4 | 4 |
| +0.20% A | 0 | 0 | 0 | 0 | 0 | 0 |
| +0.30% A | 0 | 0 | 0 | 0 | 0 | 0 |
| +0.40% A | 0 | 0 | 0 | 0 | 0 | 0 |

Algistatic finish

Without storage

| | Inhibitory zone [mm] | Colonization on the test specimens | | |
|---|---|---|---|---|
| Render, no preservative | 4 | 0 | – | – |
| +0.20% A | >18 | >18 | – | – |
| +0.30% A | >18 | >18 | – | – |
| +0.40% A | >18 | >18 | – | – |

Algistatic finish

| Test material/product | Inhibitory zone [mm] | | Colonization on the test specimens | |
|---|---|---|---|---|
| 3 month storage | No leaching | Leaching for 72 h | No leaching | Leaching for 72 h |
| Render, no preservative | 7 | 0 | – | + |
| +0.20% A | >18 | >18 | – | – |
| +0.30% A | >18 | >18 | – | – |
| +0.40% A | >18 | >18 | – | – |

5 month storage

| | A. niger | | P. funiculosum | | A. alternata | | |
|---|---|---|---|---|---|---|---|
| Product | 1 wk. | 2 wks. | 1 wk. | 2 wks. | 1 wk. | 2 wks. | Leaching |
| Render, no preservatives | 3 | 3 | 1 | 2 | 3 | 3 | No leaching |
| +0.25% benzalkonium chloride, 50% strength | 1 | 1 | 0 | 0 | 1 | 2 | No leaching |
| +0.4% A | 0 | 0 | 0 | 0 | 0 | 0 | No leaching |
| Render, no preservatives | 3 | 4 | 1 | 2 | 3 | 4 | 72 h |
| +0.25% benzalkonium chloride, 50% strength | 1 | 1 | 0 | 0 | 1 | 2 | 72 h |
| +0.4% A | 0 | 0 | 0 | 0 | 0 | 0 | 72 h |

5 month storage

| Product | Inhibitory zone in mm | Colonization on the surface |
|---|---|---|
| Render, no preservatives | >18 | — |
| +0.25% benzalkonium chloride, 50% strength | >18 | — |
| +0.4% A | >18 | — |
| Render, no preservatives | 0 | — |
| +0.25% benzalkonium chloride, 50% strength | >18 | — |
| +0.4% A | >18 | — |

The results confirm that the preservative A according to the invention is still fully effective in the render after storage for three or five months, even after exposure to leaching for 72 h.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A preservative for coating compositions, wherein said preservative is present in an aqueous and/or alcoholic based form, and comprises:
a) 8 to 18% by weight of isothiazolone;
b) 20 to 40% by weight of quaternary ammonium compound;
c) 3 to 8% by weight of stabilizer selected from the group consisting of sulphite salts, hydrogen sulphite salts, sulphite-releasing compounds and hydrogen-sulphite-releasing compounds; and at least one of
d) 10 to 18% by weight of aliphatic alcohol; and
e) 20 to 55% by weight of water;
the presence of algicidal triazine being ruled out in the preservative.

2. The preservative of claim 1, wherein said izothiazolone is selected from the group consisting of N-octylisothiazolone, 4,5-dichlorooctylisothiazolone, benzoisothiazolone, N-butylbenzoisothiazolone, and N-methylisothiazolone.

3. The preservative of claim 1, wherein said stabilizer is selected from the group consisting of sulphur dioxide, aqueous sulphur dioxide solution, alkali metal sulphites, alkali metal hydrogen sulphites and alkali metal bisulphites.

4. The preservative of claim 1, wherein said quaternary ammonium compound is selected from the group consisting of benzalkonium chloride, benzalkonium thiocyanate, benzalkonium silicate, didecyldimethylammonium salts, and polyhexamethylene biguanide salts.

5. The preservative of claim 1, wherein said preservative comprises:
a) 10 to 14% by weight of N-octylisothiazolone;
b) 24 to 33% by weight of benzalkonium chloride;
c) 4 to 7% by weight of sodium bisulphate;
d) 12 to 16% by weight of 1,2-propylene glycol; and
e) 30 to 50% by weight of water.

6. The preservative of claim 1, wherein said preservative furthermore comprises one or more functional additives selected from the group consisting of fillers, humectants, thickeners/viscosity modifiers, wetting agents, dispersants, pigment dispersers and alkalizing agents.

7. The preservative of claim 1, wherein said quaternary ammonium compound is benzalkonium chloride.

8. The preservative of claim 1, wherein said preservative comprises:
a) 10 to 14% by weight of isothiazolone;
b) 24 to 33% by weight of quaternary ammonium compound;
c) 4 to 7% by weight of stabilizer; and at least one of
d) 12 to 16% by weight of aliphatic alcohol; and
e) 30 to 50% by weight of water.

* * * * *